(12) United States Patent
Lynch et al.

(10) Patent No.: US 6,293,950 B1
(45) Date of Patent: Sep. 25, 2001

(54) RESORBABLE PIN SYSTEMS

(75) Inventors: Samuel E. Lynch, Setauket; Ralf Lange, Amagansett, both of NY (US); Hans-Peter Grimm, Oberrieden (CH)

(73) Assignee: Luitpold Pharmaceuticals, Inc., Shirley, NY (US)

( * ) Notice: Subject to any disclaimer, the term of this patent is extended or adjusted under 35 U.S.C. 154(b) by 0 days.

(21) Appl. No.: 09/231,674

(22) Filed: Jan. 15, 1999

(51) Int. Cl.[7] .................................................. A61B 17/58
(52) U.S. Cl. .............................. 606/77; 606/72; 606/104; 606/232; 411/5
(58) Field of Search .............................. 606/76, 77, 104, 606/227, 232, 73, 72, 95; 411/5, 2; 138/89; 215/356

(56) References Cited

U.S. PATENT DOCUMENTS

| | | |
|---|---|---|
| 4,171,569 | 10/1979 | Rovins . |
| 4,371,342 | 2/1983 | Filhol . |
| 4,850,847 | 7/1989 | Weissman . |
| 5,236,431 | 8/1993 | Gogolewski et al. . |
| 5,263,996 | 11/1993 | Filhol . |
| 5,275,601 | 1/1994 | Gogolewski et al. . |
| 5,398,861 | 3/1995 | Green . |
| 5,434,242 | 7/1995 | Bendix et al. . |
| 5,511,565 | 4/1996 | Syers . |
| 5,609,881 | 3/1997 | Ikada et al. . |
| 5,700,901 | 12/1997 | Hurst et al. . |
| 5,716,358 | 2/1998 | Ochoa et al. . |
| 5,720,753 | 2/1998 | Sander et al. . |
| 5,839,899 | 11/1998 | Robinson . |
| 5,902,321 | * 5/1999 | Caspari et al. ................... 606/232 |
| 5,928,236 | * 7/1999 | Augagneur et al. ............... 411/5 |

OTHER PUBLICATIONS

Claes et al., "New Bioresorbable Pin for the Reduction of Small Bony Fragments: Design, Mechanical Properties and in vitro Degradation," *Biomaterials* 17(16):1621–1626 (1996).

Doblin, et al., "A Histologic Evaluation of Localized Ridge Augmentation Utilizing DFDBA in Contribution with e–PTFE Membranes and Stainless Steel Bone Pins in Humans." *Int. J. Periodontics Restorative Dent.*, 16(2): 120–9 (1996).

Eppley, "Potential for Guided Bone Regeneration and Bone Graft Fixation with Resorbable Membranes in Pediatric Craniofacial Surgery," *J. Craniofacial Surgery*, 8(2):127–128 (1997).

Hurzeler et al., "Guided Bone Regeneration Around Exposed Implants: A New Bioresorbable Device and Bioresorbable Membrane Pins," *Practical Periodontics and Aesthetic Dentistry* 7(9): 47–49 (1995).

Mellonig et al., "Guided Bone Regeneration of Bone Defects Associated with Implants: An Evidence–Based Outcome Assessment," *Int. J. Peridontics Restorative Dent.* 15(2): 168–85 (1995).

Piatelli et al., "Bone Formation inside the Material Interstices of e–PTFE Membranes: A Light Microscopical and Histochemical Study in Man," *Biomaterials* 17(17):1725–1731 (1996).

\* cited by examiner

*Primary Examiner*—Henry J. Recla
*Assistant Examiner*—Julian W. Woo
(74) *Attorney, Agent, or Firm*—Morgan, Lewis & Bockius LLP

(57) ABSTRACT

Bioresorbable pin systems useful for the reduction of bone fragments and for fixing bioresorbable membranes to a bone are provided, particularly pins having a detachable handle and a pre-fabricated hole in the handle through which a tether may be threaded to facilitate removal of the handle once it has been detached from the pin.

12 Claims, 2 Drawing Sheets

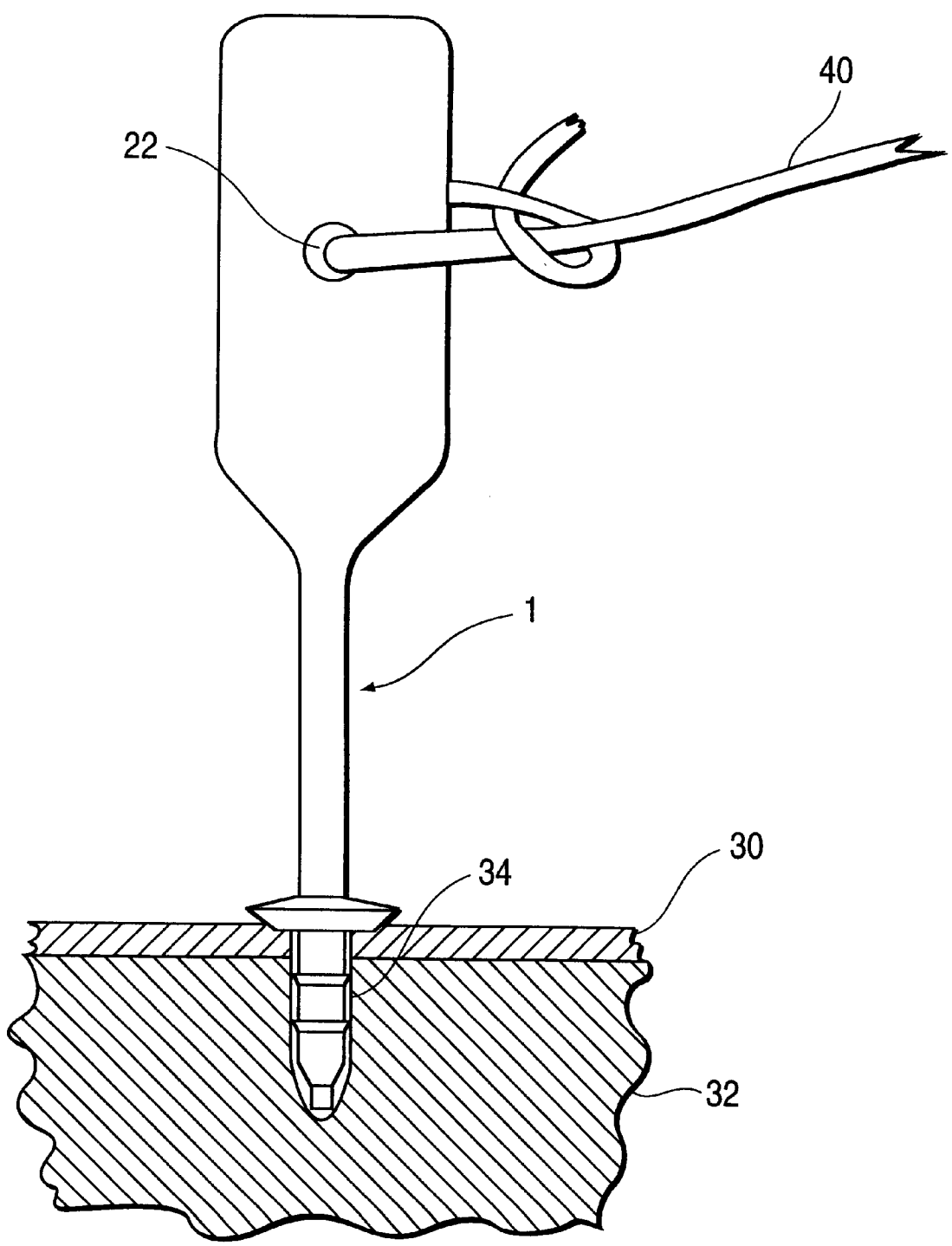

RESORBABLE PIN SYSTEMS

BACKGROUND OF THE INVENTION

1. Field of the Invention

The present invention relates to bioresorbable pin systems useful for the reduction of bone fragments and for fixing barrier membranes used in conjunction with guided bone regeneration procedures, particularly pins having a detachable handle and a pre-fabricated hole in the handle to facilitate its removal following detachment from the pin.

2. Description of the Related Art

A variety of bone and membrane fixation devices are known, including screws, pins, stables, cables and anchors. These devices are formed of a number of compositions, are available in a wide variety of shapes and have a variety of surface textures. See, e.g. U.S. Pat. No. 5,716,358 to Ochoa et al, "Directional Bone Fixation Device" (1998). However, metal implants are generally undesirable because they are associated with osteopenia and allergic reactions, and often require a second operation for their removal after the bone has healed. Accordingly, several resorbable products have been developed to provide anatomical reduction of bony fragments produced by a fracture.

A. Bioresorbable Pins

Various compositions have been used to form resorbable pins and screws, including polydioxanone and polyglycolide. These compositions tend to degrade and lose strength within days to weeks. Thus, their main use is for fast-healing fractures. Resorbable fixation devices for torn bodily material are described in U.S. Pat. No. 5,236,431 to Gogolewski et al., "Resorbable Fixation Device with Controlled Stiffness for Treating Bodily Material In Vivo and Introducer Therefore" (1993). Also known in the art are absorbable self-locking screw and plate systems for internal fixation of bone fractures and for tendon-to-bone attachment, as described, for example, in U.S. Pat. No. 5,275,601 to Gogolewski et al., "Self-locking Resorbable Screws and Plates for Internal Fixation of Bone Fractures and Tendon-to-bone Attachment" (1994).

Recently, a pin comprising 70:30 poly(L, DL-lactide), and known as the Polypin® was developed, and has improved degradation and strength characteristics appropriate for use in reducing slow-healing fractures. See, e.g., Claes et al., "New bioresorbable pin for the reduction of small bony fragments: design, mechanical properties and in vitro degradation," Biomaterials 17(16):1621–1626 (1996).

The Polypin® is an injection molded product of cylindrical shape, and having a length of 35 mm and a diameter of 2 mm. A small head, having a diameter of 2.6 mm allows the application of light compressive forces to the fragment to be fixed in place. Transverse ridges of 0.15 mm thickness provide a press fit of the pin into a pre-drilled bore hole in the bone. In use, as described by Claes et al., a drill hole of about 0.8 mm in diameter and about 2.6 mm in length in the head of the pin, is filled with an X-ray contrast marker to allow detection of the pin by X-ray.

B. Guided bone regeneration

Guided bone regeneration is a technique used to facilitate, for example, the use of dental implants in certain procedures where regeneration of bone or the incorporation of bone substitutes is desired. In the dental context, guided bone regeneration can be used successfully to promote bone formation in osseous deformities and defects in conjunction with teeth or endosseous implant placement. Osseous defects consist mainly of periodontal extraction sites, dehiscences or fenestrations, and localized ridge deformities. In addition, bone defects may either provide natural space making or be non-space making. Non-space making defects usually require bone graft materials to assist in space maintenance and to enhance bone formation. See, e.g., Mellonig, "Guided bone regeneration of bone defects associated with implants: an evidence-based outcome assessment." Int. J Periodontics Restorative Dent. 15 (2): 168–85 (1995); U.S. Pat. No. 5,839,899 to Robinson, "Method and Apparatus for Growing Jaw Bone Utilizing a Guided-tissue Regeneration Plate Support and Fixation System" (1998); and U.S. Pat. No. 5,511,565 to Syers, "Guided Bone and Tissue Generation Device and Method to Be Used During or After Dental Surgery or Jaw Surgery" (1996).

Fixation pins, as described above, are used in such guided bone regeneration procedures, with or without graft materials. For example, stainless steel bone pins have been used with decalcified freeze-dried bone allograft for localized ridge augmentation. Doblin, et al., "A Histologic Evaluation of Localized Ridge Augmentation Utilizing DFDBA in Combination with e-PTFE Membranes and Stainless Steel Bone Pins in Humans." Int. J Periodontics Restorative Dent., 16 (2): 120–9 (1996). Similarly, resorbable pins are used with various oral implants. See, e.g., Hurzeler et al., "Guided Bone Regeneration Around Exposed Implants: A New Bioresorbable Device and Bioresorbable Membrane Pins," Practical Periodontics and Aesthetic Dentistry 7(9) :37–49 (1995). Moreover, pins also are used in cranial surgery where bone regeneration is involved. See, e.g., Eppley, "Potential for Guided Bone Regeneration and Bone Graft Fixation with Resorbable Membranes in Pediatric Craniofacial Surgery," J Craniofacial Surgery, 8(2) :127–128 (1997).

In fact, one of the major uses for bioresorbable pins is to fix or stabilize barrier membranes that are themselves bioresorbable. See, Hurzeler et al., cited above. Such membranes are used to block the ingrowth of fibrous connective tissue, thereby encouraging bone cells to colonize the area adjacent to an implant. See, e.g., U.S. Pat. No. 5,609,881 to Ikada, "Biodegradable/Absorbable Barrier Membrane" (1997); and Piatelli, "Bone Formation inside the Material Interstices of e-PTFE Membranes: A Light Microscopical and Histochemical Study in Man," Biomaterials 17(17):1725–1731 (1996).

C. Pin Installation Systems

A variety of systems exist for installing pins used for various orthopedic and dental purposes. For example, the BioTack™ delivery system is useful for fixing bioabsorbable membranes. Pins come prepackaged in a sterile container with specifically designed friction fit drivers that are used to pick up and to deliver the pins to the site where bioabsorbable membranes are to be fixed for purposed of guided bone restoration.

Retentive dental pins also have been described, which comprise a lower portion that can be secured within the dentine of a tooth and an enlarged head portion to which a tooth restoration may be secured. For example, as shown in FIG. 1 of U.S. Pat. No. 5,263,996 to Filhol, "Dental Pin" (1993), a head portion (3) is connected, via a shearable connection (4) to a fixing portion (5) that is used to insert the pin into a tooth. Somewhat similar are the pins shown in FIGS. 1 and 2 of U.S. Pat. No. 4,171,569 to Rovins, "Dental Pin" (1979). In this system, a handle (4) includes fracture grooves (3) and (7) which are intended to break leaving the pin protruding from the tooth in order to anchor a superstructure on an excavated tooth.

What has been missing in the art, however, are appropriately-configured resorbable pins with handles to facilitate manual insertion of the pins, and associated techniques for using such pins, to facilitate the insertion of such pins for the fixation of bony fragments and barrier membranes, without the need for specialized tools, and that also facilitate removal of a severable handle portion after insertion of the pin portion into the bone.

SUMMARY OF THE INVENTION

The present invention has been made in view of the above circumstances and has as an object to provide a bioresorbable pin system useful for the reduction of bone fragments and for fixing bioresorbable membranes to a bone. An object of the present invention is to provide such pin systems having a pin portion having a shank and a head that is larger in diameter than the shank; and a detachable handle portion capable of being severed proximal to the head of the pin. Preferably, the pin system includes a pre-fabricated hole in the handle through which a tether may be threaded to facilitate removal of the handle once it has been detached from the pin. The handle portion of the bioresorbable pin system also preferably includes a gripping portion distal from said head, said gripping portion being sufficiently large to be manually grasped by a user to insert the pin shank into the aperture in the bone.

A further object of the present invention is to provide a bioresorbable pin system with which a pin may be manually inserted in a pre-drilled aperture in a bone without the use of specialized tools. Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

To achieve the objects and in accordance with the purpose of the invention, as embodied and broadly described herein, the invention comprises a bioresorbable pin system comprising a unitary elongated handle portion and a pin portion, the pin portion having a shank and a head, and the handle having a shaft portion directly abutting the head and being capable of being severed proximal to the head. The handle of the bioresorbable pin system may also include an enlarged end portion or tip distal from the head of said pin, with a hole pre-formed or drilled through the tip through which a string or wire may be threaded to facilitate removal of the handle portion after it has been severed from the pin portion.

It is to be understood that both the foregoing general description and the following detailed description are exemplary and explanatory only are not restrictive of the invention, as claimed. All references and other documents identified herein are incorporated by reference in their entireties.

BRIEF DESCRIPTION OF THE DRAWINGS

The accompanying drawing, which is incorporated in and constitutes a part of this specification, illustrate one embodiment of the invention and together with the description, serve to explain the principles on of the invention.

FIG. 2 is a side view of the resorbable pin system shown after insertion into a bone structure and before removal of the handle portion.

DESCRIPTION OF THE PREFERRED EMBODIMENTS

Figure 1:
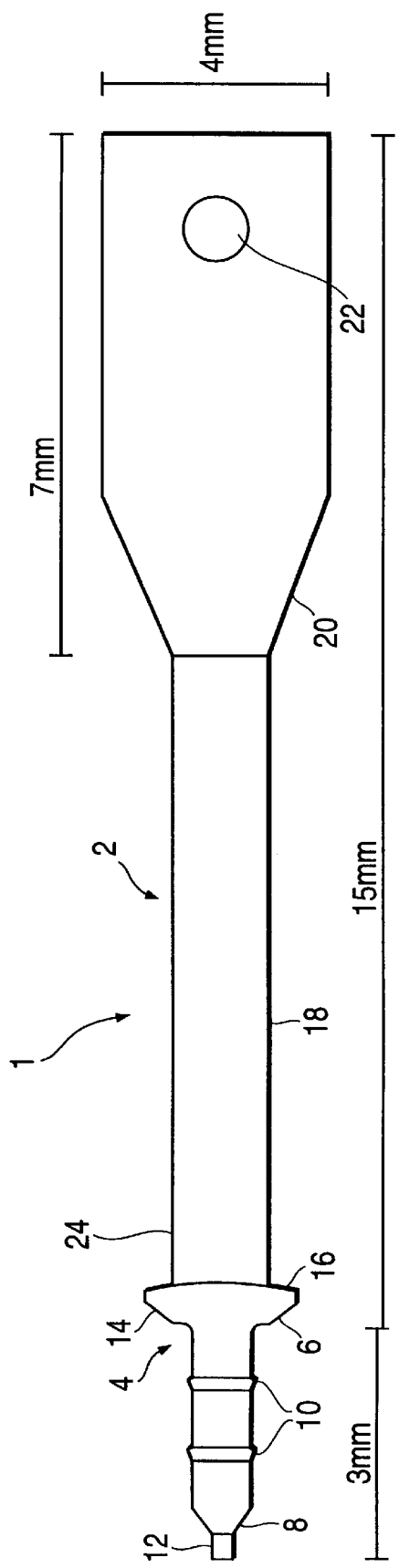
FIG. 1 is a side view of the resorbable pin system.

Reference will now be made in detail to the presently preferred embodiments of the invention, an example of which is illustrated in the accompanying drawings. In accordance with the invention, the bioresorbable pin system includes a pin having a head and a shank that can be secured within a preformed aperture in a bone, and a handle having a shaft and a tip or gripping portion that can be used to insert the pin into the aperture.

FIG. 1 show a preferred embodiment of the pin system (1) according to the present invention, which comprises an elongated handle portion (2) and a pin portion (4). The pin portion (4) further comprises a head (6) and a shank (8), the shank preferably having compressible ridges (10) and a point (12). The ridges (10) provide a press fit for the pin as it is inserted into a pre-drilled aperture in a bone. Cement or other bonding agent may be utilized in lieu of, or in addition to, the ridges to anchor the pin in a bone.

The handle portion (2) of the system further comprises a shaft (18) with a tip or gripping portion (20). Tip (20) is preferably large enough to be readily grasped between the finger tips of the user to permit the user to insert the point (12) and shank (8) of the pin portion (4) through a membrane or bone fragment and securely into a pre-formed aperture in a bone (as shown in FIG. 2). Rather than forming the entire shaft with the same thickness as the tip, most of the shaft is thinner. This facilitates severing the shaft after the pin portion has been inserted. In the illustrated embodiment, the shaft and tip are cylindrical, with a conical transition between the two cylindrical portions. However, other profiles would be suitable, including a tip portion that is flattened (e.g., that has a thickness equal to the diameter of the shaft but a greater width). Additionally, the shaft may be scored or partially cut-through, or otherwise configured, to facilitate cutting the shaft or breaking the shaft using finger pressure, thereby obviating the need for additional instrumentation to sever the handle portion from the pin portion.

The head (6) of the pin is relatively flat, has a greater diameter than the shank (8) of the pin and has a pin-side face (14) and a handle-side face (16). The pin side face (14) is configured to bear against, and provides a compressive force to, the membrane or bony fragment to be fixed to the underlying bone. It is preferred that the head protrude above the surface of the membrane or bony fragment as little as possible to avoid irritation of surrounding tissue. The head is therefore dimensioned with the minimum thickness required to sustain the desired compressive loads (in the illustrated embodiment, approximately 0.5 mm). This design criterion is therefore contrary to systems in which the head provides an anchoring function for other structure, such as the dental restoration as shown in U.S. Pat. No. 5,263,996. The pin-side face (14) of the pin (4) is thus capable of fixing, e.g., a bioresorbable membrane to a bone or fixing a bony fragment to an underlying bone.

In use, the pin (4) of resorbable pin system (1) is inserted through a hole or other opening in a bioresorbable membrane or bony fragment (30) into a predrilled aperture (34) in underlying bone (32) adjacent to the bone defect to be treated (not shown). The pin (4) may be held in place by the frictional forces between bone (32) and the ridges (10). Alternatively, or additionally, a bonding agent or other fixative may be used to further fasten the pin (4) into the aperture. After an appropriate period of time for the bonding agent, if used, to cure, the shaft (18) may be sheared or cut proximal to the handle-side face (16) of the head (6) in the vicinity of the proximal portion (24) of the shaft (18). Conventional side-cutting pliers or a dental drill may be used for such shearing or cutting.

In a preferred embodiment of the present invention, the bioresorbable pin system further includes a pre-formed hole

(22) in the tip (20) of the handle (2). In use, a tether (40), which may be any convenient thread-like material such as dental floss or wire, may be inserted through the pre-formed hole (22) before the pin portion is inserted through a bioresorbable membrane into a bone. As described, the shaft of the handle may be severed in the vicinity of the head of the pin by conventional tools. Thereafter, the handle portion of the pin system may be withdrawn, e.g., from a patient's mouth, by withdrawing the tether to which the handle portion has been threadably attached.

In a preferred embodiment of the present invention, the pin portion and handle portions are formed as a unitary device and are made of the same polymer composition. As illustrated in FIG. 1, the shank of the pin is approximately 3.0 mm in length and the head of the pin is about 0.5 mm in thickness (measured along the axis of the pin). The shaft of the handle portion is about 8.0 mm and the tip portion of the handle is about 7.0 mm in length. The diameter of the shank of the pin is about 0.8 mm and the ridges on the shank are about 1.0 mm in diameter. The head of the pin is about 2.0 mm in diameter, and the diameter of the tip is about 4.0 mm, tapering down to about 2.0 mm where the tip meets the shaft.

The bioresorbable pin system of the present invention may be formulated of any composition known in the art as being appropriate for reabsorption. However, the formulation utilized must be sufficiently strong to allow the pin to be pressed into pre-drilled holes. A preferred formulation is 70:30 poly(L, DL-lactide). Other bioresorbable formulations are known in the art.

It will be apparent to those skilled in the art that various modifications and variations can be made in the geometry and dimensions of the pin of the present invention and in construction of this bioresorbable pin system without departing from the scope or spirit of the invention. For example, the length and diameter of the shank and the diameter and thickness of the head may be varied to suit different applications, e.g., different thicknesses of membranes or bony fragments to be fixed to the underlying bone. The number, profile, position, and dimensions of ridges may be varied, and the handle may be scored in the vicinity of the head of the pin to facilitate severing the handle from the pin.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A bioresorbable bone pin system for insertion into an aperture in a bone to fix a bioresorbable membrane or bony fragment to the bone, comprising:

a pin portion having a shank and a head larger in diameter than said shank; and a handle portion coupled to said head and capable of being severed proximal to said head;

wherein said handle portion includes an elongated shaft portion proximal to said head and a gripping portion distal from said head, said gripping portion being sufficiently large to be manually grasped by a user to insert the pin shank into the aperture in the bone, and said shaft portion being smaller in diameter than said gripping portion; and wherein said handle portion further includes a hole through which a tether may be inserted.

2. The bioresorbable bone pin system of claim 1, wherein said hole is formed in said gripping portion.

3. The bioresorbable bone pin system of claim 1, wherein said shank includes ridges for frictionally engaging the aperture in the bone to retain the pin to the bone.

4. The bioresorbable bone pin system of claim 1, wherein said head is dimensioned to lie substantially flush with the membrane of bony fragment to be fixed to the bone.

5. A bioresorbable bone pin system for insertion into an aperture in a bone to fix a bioresorbable membrane or bony fragment to the bone, comprising:

a pin portion having a shank and a head larger in diameter than said shank; and a handle portion coupled to said head and capable of being severed proximal to said head;

wherein said handle portion includes an elongated shaft portion proximal to said head and a gripping portion distal from said head, said gripping portion being sufficiently large to be manually grasped by a user to insert the pin shank into the aperture in the bone and having a hole through which a tether may be inserted.

6. The bioresorbable bone pin system of claim 5, wherein said shank includes ridges for frictionally engaging the aperture in the bone to retain the pin to the bone.

7. The bioresorbable bone pin system of claim 5, wherein said head is dimensioned to lie substantially flush with the membrane of bony fragment to be fixed to the bone.

8. A method of fixing a bioresorbable membrane or bony fragment to a bony structure with a bioresorbable pin having a pin shank, a pin head, and a handle with an elongated shaft portion coupled to the pin head at one end thereof and a gripping portion at the other end thereof, the gripping portion being sufficiently large to be manually grasped by a user and having a hole through which a tether may be inserted, comprising the steps of:

inserting a tether through the hole;

inserting the pin shank through the membrane or fragment into an aperture in the bone;

securing the pin shank to the bone;

severing the shaft from the head; and after severing the shaft from the head, withdrawing the handle with the tether.

9. The method of claim 8 wherein said step of securing the pin shank to the bone comprises frictionally engaging ridges on the pin shank with the aperture.

10. A method of fixing a bioresorbable membrane or bony fragment to a bony structure with a bioresorbable pin having a pin shank, a pin head, and a handle with an elongated shaft portion coupled to the pin head at one end thereof and a gripping portion at the other end thereof, the gripping portion being sufficiently large to be manually grasped by a user, and said shaft portion being smaller in diameter than said gripping portion, wherein the handle includes a hole, comprising the steps of:

inserting a tether through the hole;

inserting the pin shank through the membrane or fragment into an aperture in the bone;

securing the pin shank to the bone;

severing the shaft from the head, and, after severing the shaft from the head, withdrawing the handle with the tether.

11. The method of claim 10 wherein said step of securing the pin shank to the bone comprises frictionally engaging ridges on the pin shank with the aperture.

12. The method of claim 10, wherein said severing is done manually.

* * * * *